(12) United States Patent
Nappa et al.

(10) Patent No.: US 8,148,586 B2
(45) Date of Patent: Apr. 3, 2012

(54) CATALYTIC PRODUCTION PROCESSES FOR MAKING TETRAFLUOROPROPENES AND PENTAFLUOROPROPENES

(75) Inventors: Mario Joseph Nappa, Newark, DE (US); Velliyur Nott Mallikarjuna Rao, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/152,405

(22) Filed: Jun. 3, 2011

(65) Prior Publication Data

US 2011/0237845 A1 Sep. 29, 2011

Related U.S. Application Data

(63) Continuation of application No. 12/373,594, filed as application No. PCT/US2007/015751 on Jul. 11, 2007, now Pat. No. 7,982,073.

(60) Provisional application No. 60/830,939, filed on Jul. 13, 2006.

(51) Int. Cl.
*C07C 17/25* (2006.01)

(52) U.S. Cl. ........................................ 570/156; 570/157

(58) Field of Classification Search ........................ None
See application file for complete search history.

(56) References Cited

U.S. PATENT DOCUMENTS

| | | | |
|---|---|---|---|
| 2,461,523 A | 2/1949 | Coffman et al. | |
| 3,258,500 A | 6/1966 | Swamer et al. | |
| 4,828,818 A | 5/1989 | Carlson et al. | |
| 5,036,036 A | 7/1991 | Lerou | |
| 5,396,000 A | 3/1995 | Nappa et al. | |
| 5,679,875 A | 10/1997 | Aoyama et al. | |
| 6,455,745 B1 * | 9/2002 | Takahashi et al. | 570/166 |
| 7,388,117 B2 | 6/2008 | Miller et al. | |
| 7,423,188 B2 | 9/2008 | Miller et al. | |
| 7,476,771 B2 | 1/2009 | Miller et al. | |
| 2005/0245773 A1 | 11/2005 | Mukhopadhyay et al. | |
| 2006/0106263 A1 | 5/2006 | Miller et al. | |
| 2007/0100175 A1* | 5/2007 | Miller et al. | 570/178 |
| 2008/0058562 A1* | 3/2008 | Petrov et al. | 570/168 |
| 2009/0127496 A1 | 5/2009 | Rao et al. | |

FOREIGN PATENT DOCUMENTS

| | | |
|---|---|---|
| EP | 0234002 A1 | 9/1987 |
| EP | 234002 A1 * | 9/1987 |
| EP | 0726243 A1 | 8/1996 |
| EP | 0974571 A | 1/2000 |

OTHER PUBLICATIONS

Kohne, A., et al, "Heterogeneous Catalyzed Synthesis of 1,1,1,2-Tetrafluoroethane from 1,1,1,2-Tetrachloroethane—Thermodynamics and Reaction Pathways," Journal of Fluorine Chemistry, 75, (1995) pp. 103-110.

* cited by examiner

*Primary Examiner* — Sudhakar Katakam

(57) ABSTRACT

A process is disclosed for making $CF_3CF=CHF$. The process involves contacting at least one hexafluoropropane selected from the group consisting of $CF_3CF_2CH_2F$ and $CF_3CHFCHF_2$ with a chromium oxyfluoride catalyst in a reactor to obtain a product mixture comprising $CF_3CF=CHF$, and recovering $CF_3CF=CHF$ from the product mixture.

A process is disclosed for making $CF_3CH=CHF$. The process involves contacting $CF_3CH_2CHF_2$ with a chromium oxyfluoride catalyst in a reactor to obtain a product mixture comprising $CF_3CH=CHF$, and recovering $CF_3CH=CHF$ from the product mixture.

A process is disclosed for making $CF_3CF=CH_2$. The process involves contacting $CF_3CF_2CH_3$ with a chromium oxyfluoride catalyst in a reactor to obtain a product mixture comprising $CF_3CF=CH_2$, and recovering $CF_3CF=CH_2$ from the product mixture.

17 Claims, No Drawings

CATALYTIC PRODUCTION PROCESSES FOR MAKING TETRAFLUOROPROPENES AND PENTAFLUOROPROPENES

CROSS-REFERENCE TO RELATED APPLICATION

This application is a Continuation of application Ser. No. 12/373,594 filed Feb. 23, 2009 which represents a national filing under 35 U.S.C. 371 of International Application No. PCT/US07/15751 filed Jul. 11, 2007 and claims priority of U.S. Patent Application 60/830,939 filed Jul. 13, 2006.

BACKGROUND

1. Field of the Disclosure

The disclosure herein relates in general to processes for the chromium oxyfluoride catalyzed dehydrofluorination of hydrofluorocarbons to make hydrofluoroolefins. More particularly, the disclosure herein relates to the chromium oxyfluoride catalyzed dehydrofluorination of hydrofluoropropanes to make hydrofluoropropenes.

2. Description of Related Art

As a result of the Montreal Protocol phasing out ozone depleting chlorofluorocarbons (CFCs) and hydrochlorofluorocarbons (HCFCs), industry has been working for the past few decades to find replacement refrigerants. The solution for most refrigerant producers has been the commercialization of hydrofluorocarbon (HFC) refrigerants. The new hydrofluorocarbon refrigerants, HFC-134a being the most widely used at this time, have zero ozone depletion potential and thus are not affected by the current regulatory phase out as a result of the Montreal Protocol. The production of other hydrofluorocarbons for use in applications such as solvents, blowing agents, cleaning agents, aerosol propellants, heat transfer media, dielectrics, fire extinguishants and power cycle working fluids has also been the subject of considerable interest.

There is also considerable interest in developing new refrigerants with reduced global warming potential for the mobile air-conditioning market.

Tetrafluoropropenes and pentafluoropropenes, both having zero ozone depletion and low global warming potential, have been identified as potential refrigerants. European Patent Application EP 726 243 discloses a process for the manufacture of 1,2,3,3,3-pentafluoropropene (HFC-1225ye) by the dehydrofluorination of 1,1,1,2,3,3-hexafluoropropane (HFC-236ea). The dehydrofluorination is done in the vapor phase in the presence of a trivalent chromium oxide or partly fluorinated trivalent chromium oxide catalyst.

There is a need for new manufacturing processes for the production of tetrafluoropropenes and pentafluoropropenes.

HFC-1225ye may exist as one of two configurational isomers, E or Z, which boils at different temperatures. It has been identified that Z isomer is preferable as a refrigerant. Thus, there is a need for manufacturing processes for the HFC-1225ye productions with a high Z/E ratio.

SUMMARY

A process has been provided to produce HFC-1225ye. The process comprises: (a) contacting at least one hexafluoropropane selected from the group consisting of 1,1,1,2,2,3-hexafluoropropane (HFC-236cb) and HFC-236ea with a chromium oxyfluoride catalyst in a reactor to obtain a product mixture comprising HFC-1225ye which includes Z-HFC-1225ye and E-HFC-1225ye and (b) recovering said HFC-1225ye from said product mixture.

A process has also been provided to produce 1,3,3,3-tetrafluoropropene (HFC-1234ze). The process comprises: (a) contacting 1,1,1,3,3-pentafluoropropane (HFC-245fa) with a chromium oxyfluoride catalyst in a reactor to obtain a product mixture comprising HFC-1234ze; and (b) recovering said HFC-1234ze from said product mixture.

A process has also been provided to produce 2,3,3,3-tetrafluoropropene (HFC-1234yf). The process comprises: (a) contacting 1,1,1,2,2-pentafluoropropane (HFC-245cb) with a chromium oxyfluoride catalyst in a reactor to obtain a product mixture comprising HFC-1234yf; and (b) recovering said HFC-1234yf from said product mixture.

The foregoing general description and the following detailed description are exemplary and explanatory only and are not restrictive of the invention, as defined in the appended claims.

DETAILED DESCRIPTION

Before addressing details of embodiments described below, some terms are defined or clarified.

HFC-1225ye may exist as one of two configurational isomers, E or Z. HFC-1225ye as used herein refers to the isomers, E-HFC-1225ye (CAS reg no. 5595-10-8) or Z-HFC-1225ye (CAS reg. no. 5528-43-8), as well as any combinations or mixtures of such isomers.

HFC-1234ze can also exist as one of two configurational isomers, E or Z. HFC-1234ze as used herein refers to the isomers, E-HFC-1234ze or Z-HFC-1234ze, as well as any combinations or mixtures of such isomers.

The term "hexafluoropropane" is intended to mean a partially fluorinated propane represented by the formula $C_3H_2F_6$. In one embodiment of this invention, a hexafluoropropane is selected from the group consisting of HFC-236cb and HFC-236ea.

The term "a chromium oxyfluoride catalyst" is intended to mean a chromium oxyfluoride represented by formula $Cr_2O_xF_y$ wherein $x+y/2=3$.

The term "amorphous" is intended to mean that there is no substantial peak in a X-ray diffraction pattern of the subject solid.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

The chromium oxyfluoride catalysts can be made by treating $Cr_2O_3$ with HF, $CCl_3F$ or hydrofluorocarbons. In one embodiment of this invention, a chromium oxyfluoride catalyst is made by treating dry $Cr_2O_3$ with a fluorination agent such as $CCl_3F$ or HF. This treatment can be accomplished by placing the $Cr_2O_3$ in a suitable container (which can be the reactor to be used to perform the dehydrofluorination reaction) and thereafter passing HF over the dry $Cr_2O_3$ for a suitable period of time (e.g., about 15 to 300 minutes) at a suitable temperature (e.g., about 200° C. to 450° C.), such as what described in Example 1.

In another embodiment of this invention, a chromium oxyfluoride catalyst is made by treating $Cr_2O_3$ with a hydrofluorocarbon at an elevated temperature.

In another embodiment of this invention, a chromium oxyfluoride catalyst is made in situ. For example, the reactant HFC-236cb, HFC-236ea, HFC-245fa or HFC-245cb can be employed in the formation of a chromium oxyfluoride catalyst by heating together with $Cr_2O_3$ in the reactor.

$Cr_2O_3$ is commercially available from Engelhard Corporation (101 Wood Avenue, P.O. Box 770, Iselin, N.J. 08830-0770).

$Cr_2O_3$ can also be prepared by pyrolysis of ammonium dichromate as disclosed in U.S. Pat. No. 5,036,036, which is incorporated herein by reference.

$Cr_2O_3$ can also be prepared by the reaction of chromium (VI) oxide with a reducing solvent, such as methanol, as disclosed in U.S. Pat. No. 4,828,818, which is incorporated herein by reference.

$Cr_2O_3$ can also be prepared by reducing chromium (VI) oxide in water with a suitable reducing agent, such as ethanol, as disclosed in U.S. Pat. No. 3,258,500, which is incorporated herein by reference.

The amount of potassium and other alkali metals in $Cr_2O_3$ can be reduced by a water washing step as disclosed in U.S. Pat. No. 5,036,036.

In one embodiment of this invention, the chromium oxyfluoride catalyst has surface areas of about 20 $m^2/g$ to about 500 $m^2/g$.

In another embodiment of this invention, the chromium oxyfluoride catalyst has surface areas of about 40 $m^2/g$ to about 350 $m^2/g$.

In another embodiment of this invention, the chromium oxyfluoride catalyst has surface areas of about 60 $m^2/g$ to about 300 $m^2/g$.

In another embodiment of this invention, the chromium oxyfluoride catalyst has surface areas of about 100 $m^2/g$ to about 300 $m^2/g$.

In one embodiment of this invention, the chromium oxyfluoride catalyst contains an alkali metal content of about 2000 ppm or less.

In another embodiment of this invention, the chromium oxyfluoride catalyst contains an alkali metal content of about 300 ppm or less.

In another embodiment of this invention, the chromium oxyfluoride catalyst contains an alkali metal content of about 100 ppm or less.

In one embodiment of this invention, the chromium oxyfluoride catalyst is amorphous.

In another embodiment of this invention, the chromium oxyfluoride catalyst is prepared from crystalline $\alpha$-$Cr_2O_3$.

A process has been provided to produce HFC-1225ye. The process comprises: (a) contacting at least one hexafluoropropane selected from the group consisting of 1,1,1,2,2,3-hexafluoropropane (HFC-236cb) and HFC-236ea with a chromium oxyfluoride catalyst in a reactor to obtain a product mixture comprising HFC-1225ye; and (b) recovering said HFC-1225ye from said product mixture.

In one embodiment of this invention, the molar ratio of Z-HFC-1225ye to E-HFC-1225ye in the product mixture is at least 6.0.

In another embodiment of this invention, the molar ratio of Z-HFC-1225ye to E-HFC-1225ye in the product mixture is at least 7.0.

In another embodiment of this invention, the molar ratio of Z-HFC-1225ye to E-HFC-1225ye in the product mixture is at least 8.0.

In one embodiment of this invention, HFC-1225ye present in the product mixture may be separated from the other components of the product mixture and unreacted starting materials by fractional distillation. When HF is also present in the product mixture, this separation can also include isolation of azeotrope or near azeotrope of HFC-1225ye and HF and further processing to produce HF-free HFC-1225ye by using procedures similar to that disclosed in US Patent Publication US 2006/0106263 A1, which is incorporated herein by reference.

U.S. Pat. No. 7,388,117, incorporated herein by reference, discloses an azeotrope or near-azeotrope composition of Z-HFC-1225ye and HF.

Unreacted starting material can be recycled to the reactor for the production of additional HFC-1225ye. In one embodiment of this invention, HFC-236cb and/or HFC-236ea is recovered from the product mixture by fractional distillation and recycled to the reactor.

A process has also been provided to produce HFC-1234ze. The process comprises: (a) contacting HFC-245fa with a chromium oxyfluoride catalyst in a reactor to obtain a product mixture comprising HFC-1234ze; and (b) recovering said HFC-1234ze from said product mixture.

In one embodiment of this invention, HFC-1234ze present in the product mixture may be separated from the other components of the product mixture and unreacted starting materials by fractional distillation. When HF is also present in the product mixture, this separation can also include isolation of azeotrope or near azeotrope of HFC-1234ze and HF and further processing to produce HF-free HFC-1234ze by using procedures similar to that disclosed in US Patent Publication US 2006/0106263 A1.

U.S. Pat. No. 7,423,188, incorporated herein by reference, discloses an azeotrope or near-azeotrope composition of the E-isomer of HFC-1234ze and HF. U.S. Pat. No. 7,722,781, incorporated herein by reference, discloses an azeotrope or near-azeotrope composition of the Z-isomer of HFC-1234ze and HF.

Unreacted starting material can be recycled to the reactor for the production of additional HFC-1234ze. In one embodiment of this invention, HFC-245fa is recovered from the product mixture by fractional distillation and recycled to the reactor.

A process has also been provided to produce HFC-1234yf. The process comprises: (a) contacting HFC-245cb with a chromium oxyfluoride catalyst in a reactor to obtain a product mixture comprising HFC-1234yf; and (b) recovering said HFC-1234yf from said product mixture.

In one embodiment of this invention, HFC-1234yf present in the product mixture may be separated from the other components of the product mixture and unreacted starting materials by fractional distillation. When HF is also present in the product mixture, this separation can also include isolation of azeotrope or near azeotrope of HFC-1234yf and HF and further processing to produce HF-free HFC-1234yf by using procedures similar to that disclosed in US Patent Publication US 2006/0106263 A1.

U.S. Pat. No. 7,476,771, incorporated herein by reference, discloses an azeotrope or near-azeotrope composition of HFC-1234yf and HF.

Unreacted starting material can be recycled to the reactor for the production of additional HFC-1234yf. In one embodiment of this invention, HFC-245cb is recovered from the product mixture by fractional distillation and recycled to the reactor.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims.

The temperature employed in the reaction processes above typically ranges from about 200° C. to 500° C. In one embodiment of the invention, the temperature employed in the reaction processes above ranges from about 300° C. to 400° C.

Reaction time for the processes above is not critical and typically ranges from about 1 second to about 1000 seconds. In one embodiment of the invention, the reaction temperature ranges from about 5 seconds to about 100 seconds.

The reaction pressure for the processes above can be subatmospheric, atmospheric or superatmospheric. In one embodiment of the invention, the reaction pressure is near atmospheric.

Optionally, the reactions in the processes above can be done in the presence of oxygen. In one embodiment of the invention, the reactions in the processes above is done in the presence of air. In another embodiment of the invention, air is co-fed with the reactant into the reactor.

Optionally, the reactions in the processes above can be done in the presence of inert gases such as nitrogen, helium, argon, or their mixtures thereof. In one embodiment of the invention, the inert gas is co-fed with the reactant into the reactor. In another embodiment of the invention, the inert gas is nitrogen.

The reactors, distillation columns, and their associated feed lines, effluent lines, and associated units used in applying the processes of embodiments of this invention should be constructed of materials resistant to corrosion. Typical materials of construction include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

EXAMPLES

The concepts described herein will be further described in the following examples, which do not limit the scope of the invention described in the claims.

Example 1

Example 1 demonstrates a method for preparing a chromium oxyfluoride catalyst. Example 1 also demonstrates that HFC-1225ye was produced with high Z/E ratio. Example 1 also demonstrates that the activity of the chromium oxyfluoride catalyst can be recovered by air treatment.

Chromium oxide was prepared by the pyrolysis of ammonium dichromate as described in U.S. Pat. No. 5,036,036. The chromium oxide contained less than 100 ppm of alkali metals, had an alpha chromium oxide structure and a surface area of 40-55 $m^2$/gm.

An Inconel tube (⅝ inch OD) was filled with 5 cc (7.18 gm) of chromium oxide pellets, crushed and sieved to 12/20 mesh. The chromium oxide was heated to 200° C. for 15 minutes under a purge of $N_2$ (50 sccm, $8.33 \times 10^{-7}$ $m^3$/s). Then the temperature was raised to 325° C. for 10 minutes, to 400° for 20 minutes, and lowered to 300° C. for 35 minutes. The temperature was raised to 325° C. for 60 minutes while flowing $N_2$ (35 sccm, $5.83 \times 10^{-7}$ $m^3$/s) and HF (12 sccm, $2.00 \times 10^{-7}$ $m^3$/s) for 35 minutes. While maintaining this flow, the temperature was raised to 350° C. for 60 minutes, to 375° C. for 90 minutes, to 400° C. for 30 minutes, and to 425° C. for 40 minutes. While maintaining the temperature at 425° C., the flow of $N_2$ was reduced to 25 sccm ($4.17 \times 10^{-7}$ $m^3$/s) and HF raised to 20 sccm ($3.33 \times 10^{-7}$ $m^3$/s) for 20 minutes. Then the flow of $N_2$ was reduced to 15 sccm ($2.50 \times 10^{-7}$ $m^3$/s) and HF raised to 28 sccm ($4.67 \times 10^{-7}$ $m^3$/s) for 20 minutes. Then the flow of $N_2$ was reduced to 5 sccm ($8.33 \times 10^{-8}$ $m^3$/s) and HF raised to 36 sccm ($6.00 \times 10^{-7}$ $m^3$/s) for 20 minutes.

After the HF treatment, the tube temperature was lowered to 348° C. and HFC-236cb was flowed through the tube at 21.1 sccm ($3.52 \times 10^{-7}$ $m^3$/s) and $N_2$ at 5.0 sccm ($8.33 \times 10^{-8}$ $m^3$/s). The contact time of the HFC-236cb with the catalyst is 30 seconds. The product mixture was analyzed by GC-MS. The analytical results were given in units of GC area % in Table 1 below. Small amounts of other products, having GC area % less than 0.5, were not included in Table 1. After 26 hours, there was a degradation of performance. Treatment of the catalyst with air returned the activity of the catalyst to it's original activity. In Table 1 below, the catalyst was treated with air in the tube after 26 hours run time. The catalyst was then reactivated with HF in the tube. The run time counting was stopped during the air treatment and HF reactivation and was resumed when the HFC-236cb flow started again.

TABLE 1

| Run Time (Hours) | Unreacted HFC-236cb | Z-HFC-1225ye | E-HFC-1225ye | HFC-236ea |
|---|---|---|---|---|
| 2 | 59.5 | 32.7 | 4.2 | 3.5 |
| 26 | 76.2 | 19.7 | 2.6 | 1.5 |
| Treatment with Air, then HF | | | | |
| 29 | 59.9 | 32.2 | 3.9 | 3.6 |

The air treatment is shown in Table 2. The flows of air and nitrogen are in sccm.

TABLE 2

| Run Time (minutes) | Air | Nitrogen | Treatment Temperature |
|---|---|---|---|
| 0 | 0.0 | 50.0 | 240 |
| 1 | 0.0 | 45.0 | 425 |
| 15 | 5.0 | 45.0 | 425 |
| 75 | 0.0 | 45.0 | 425 |
| 105 | 2.5 | 45.0 | 425 |
| 165 | 5.0 | 45.0 | 425 |
| 195 | 10.0 | 40.0 | 425 |
| 225 | 20.0 | 30.0 | 425 |
| 315 | 30.0 | 0.0 | 425 |
| 405 | 0.0 | 50.0 | 240 |

After the air treatment above, the catalyst was reactivated with HF as described below.

The catalyst was heated to 200° C. for 15 minutes under a purge of $N_2$ (50 sccm, $8.33\times10^{-7}$ m³/s). Then the temperature was raised to 325° C. for 10 minutes, to 400° C. for 20 minutes, and lowered to 300° C. for 35 minutes. The temperature was then raised to 325° C. for 60 minutes while flowing $N_2$ (35 sccm, $5.83\times10^{-7}$ m³/s) and HF (12 sccm, $2.00\times10^{-7}$ m³/s) for 35 minutes. While maintaining this flow, the temperature was raised to 350° C. for 60 minutes, 375° C. for 90 minutes, 400° C. for 30 minutes, and 425° C. for 40 minutes. The flow of $N_2$ was reduced to 25 sccm ($4.17\times10^{-7}$ m³/s) and HF raised to 20 sccm ($3.33\times10^{-7}$ m³/s) for 20 minutes. Then the flow of $N_2$ was reduced to 15 sccm ($2.50\times10^{-7}$ m³/s) and HF raised to 28 sccm ($4.67\times10^{-7}$ m³/s) for 20 minutes. Then the flow of $N_2$ was reduced to 5 sccm ($8.33\times10^{-8}$ m³/s) and HF raised to 36 sccm ($6.00\times10^{-7}$ m³/s) for 20 minutes.

Example 2

Comparative

Example 2 demonstrates that the chromium oxyfluoride catalyst prepared as described below is not as effective as the one in Example 1.

$Cr_2O_3$ in this Example was a hydrated form of hexagonal chromium oxide also known as Guignet's Green. It contained high levels of alkali metals (Na, 3400 ppm; K, 150 ppm), and B (1.4%), Ca (0.5%), Fe (0.2%), Mg (0.1%), as well as Ba, Mn, V, and Zn. The surface area of this $Cr_2O_3$ was 100-150 m²/gm.

An Inconel tube (⅝ inch OD) was filled with 13 cc (10.32 gm) of chromium oxide pellets, crushed and sieved to 12/20 mesh. The catalyst was heated to 200° C. for 15 minutes under a purge of $N_2$ (50 sccm, $8.33\times10^{-7}$ m³/s). Then the temperature was raised to 325° C. for 10 minutes, to 400° C. for 20 minutes, and lowered to 300° C. for 35 minutes. The temperature was then raised to 325° C. for 60 minutes while flowing $N_2$ (35 sccm, $5.83\times10^{-7}$ m³/s) and HF (12 sccm, $2.00\times10^{-7}$ m³/s) for 35 minutes. While maintaining this flow, the temperature was raised to 350° C. for 60 minutes, 375° C. for 90 minutes, 400° C. for 30 minutes, and 425° C. for 40 minutes. The flow of $N_2$ was reduced to 25 sccm ($4.17\times10^{-7}$ m³/s) and HF raised to 20 sccm ($3.33\times10^{-7}$ m³/s) for 20 minutes. Then the flow of $N_2$ was reduced to 15 sccm ($2.50\times10^{-7}$ m³/s) and HF raised to 28 sccm ($4.67\times10^{-7}$ m³/s) for 20 minutes. Then the flow of $N_2$ was reduced to 5 sccm ($8.33\times10^{-8}$ m³/s) and HF raised to 36 sccm ($6.00\times10^{-7}$ m³/s) for 20 minutes.

After the HF treatment, the tube temperature was lowered to 373° C. and HFC-236cb was flowed through the tube at 13.0 sccm ($2.17\times10^{-7}$ m³/s). The contact time of the HFC-236cb with the catalyst is 60 seconds. The product mixture was analyzed by GC-MS. The analytical results were given in units of GC area % in Table 3 below. Small amounts of other products, having GC area % less than 0.5, were not included in Table 3.

TABLE 3

| Run Time (Hours) | Unreacted HFC-236cb | Z-HFC-1225ye | E-HFC-1225ye | HFC-236ea |
|---|---|---|---|---|
| 6 | 98.4 | 1.3 | 0 | 0 |

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A process comprising: (a) contacting 1,1,1,2,2-pentafluoropropane with a chromium oxyfluoride catalyst in a reactor to obtain a product mixture comprising 2,3,3,3-tetrafluoropropene; and (b) recovering said 2,3,3,3-tetrafluoropropene from said product mixture; wherein said chromium oxyfluoride catalyst is represented by formula $Cr_2O_xF_y$, wherein $x+y/2=3$.

2. The process of claim 1 wherein said catalyst has surface areas of about 20 m²/g to about 500 m²/g.

3. The process of claim 1 wherein said catalyst has surface areas of about 40 m²/g to about 350 m²/g.

4. The process of claim 1 wherein said catalyst has surface areas of about 60 m²/g to about 300 m²/g.

5. The process of claim 1 wherein said catalyst has surface areas of about 100 m²/g to about 300 m²/g.

6. The process of claim 1 wherein said catalyst contains an alkali metal content of about 2000 ppm or less.

7. The process of claim 1 wherein said catalyst contains an alkali metal content of about 300 ppm or less.

8. The process of claim 1 wherein said catalyst contains an alkali metal content of about 100 ppm or less.

9. The process of claim 1 wherein said contact is conducted at a temperature of from about 200° C. to about 500° C.

10. The process of claim 1 wherein said contact is conducted at a temperature of from about 300° C. to about 400° C.

11. The process of claim 1 wherein said catalyst is amorphous.

12. The process of claim 1 wherein said catalyst is prepared from crystalline α-$Cr_2O_3$.

13. The process of claim 1 wherein said catalyst is produced in situ.

14. The process of claim 1 wherein an inert gas is also fed to said reactor.

15. The process of claim 14 wherein said inert gas is nitrogen.

16. The process of claim 1 wherein a gas comprising oxygen is also fed to said reactor.

17. The process of claim 16 wherein said gas is air.

* * * * *